(12) United States Patent
Otsubo et al.

(10) Patent No.: US 9,078,788 B2
(45) Date of Patent: Jul. 14, 2015

(54) DISPOSABLE WEARING ARTICLE

(75) Inventors: Toshifumi Otsubo, Kanonji (JP);
Tatsuya Hashimoto, Kanonji (JP);
Mariko Yamashita, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 209 days.

(21) Appl. No.: 13/521,496

(22) PCT Filed: Jan. 17, 2011

(86) PCT No.: PCT/JP2011/050664
§ 371 (c)(1),
(2), (4) Date: Jul. 11, 2012

(87) PCT Pub. No.: WO2011/090000
PCT Pub. Date: Jul. 28, 2011

(65) Prior Publication Data
US 2012/0283682 A1  Nov. 8, 2012

(30) Foreign Application Priority Data
Jan. 19, 2010 (JP) .................. 2010-009520

(51) Int. Cl.
*A61F 13/15* (2006.01)
*A61F 13/49* (2006.01)
(Continued)

(52) U.S. Cl.
CPC ..... *A61F 13/49009* (2013.01); *A61F 13/49058* (2013.01); *A61F 13/51496* (2013.01); *A61F 2013/8497* (2013.01)

(58) Field of Classification Search
CPC ............... A61F 13/42; A61F 2013/422; A61F 2013/429; A61F 2013/8497; A61F 13/52496; A61F 13/54961
USPC .......................................... 604/361
See application file for complete search history.

(56) References Cited

U.S. PATENT DOCUMENTS 6,352,528 B1 * 3/2002 Weber et al. ............. 604/385.03
6,354,984 B1 * 3/2002 Hensley et al. ................. 493/11
(Continued)

FOREIGN PATENT DOCUMENTS

JP     2000510377 A    8/2000
JP     2004513680 A    5/2004
(Continued)

OTHER PUBLICATIONS

Internatioanl Search Report and Written Opinion for PCT/JP2011/050664, date Apr. 12, 2011.
Supplementary European Search Report issued May 27, 2014, corresponds to European patent application No. 11734606.4.

*Primary Examiner* — Lynne Anderson
(74) *Attorney, Agent, or Firm* — Lowe Hauptman & Ham, LLP

(57) ABSTRACT

The present invention provides a disposable wearing article having a position indicator mark formed on a crotch member and overlapped by front and rear waist members. Front and rear waist members overlap front and rear ends, respectively, of a crotch member and are bonded thereto to define first and second overlapping regions and an intermediate region extending between these first and second overlapping regions. A position indicator mark is formed in the first overlapping region, a graphic of fish is portrayed as a crotch graphic element in the second overlapping region and graphics of fish are portrayed in the intermediate region as crotch graphic elements. In the first overlapping region, a front waist sheet of the front waist member overlaps a front graphic film on which a graphic of penguin is portrayed as a front graphic element which, in turn, overlaps the position indicator mark.

7 Claims, 8 Drawing Sheets

(51) Int. Cl.
*A61F 13/514* (2006.01)
*A61F 13/84* (2006.01)

(56) References Cited

U.S. PATENT DOCUMENTS

| | | | |
|---|---|---|---|
| 7,530,972 B2* | 5/2009 | Ando et al. | 604/385.27 |
| 7,851,666 B2* | 12/2010 | Belau et al. | 604/358 |
| 2003/0073966 A1 | 4/2003 | Sosalla et al. | |
| 2003/0105443 A1 | 6/2003 | Ohnishi et al. | |
| 2003/0229325 A1 | 12/2003 | Belau et al. | |
| 2003/0233081 A1 | 12/2003 | Belau et al. | |
| 2004/0243083 A1 | 12/2004 | Matsuda et al. | |
| 2005/0125180 A1* | 6/2005 | Miller et al. | 702/94 |
| 2009/0254058 A1* | 10/2009 | Shiriike et al. | 604/385.01 |
| 2011/0192012 A1* | 8/2011 | Trennepohl et al. | 29/458 |

FOREIGN PATENT DOCUMENTS

| | | |
|---|---|---|
| JP | 2005505382 A | 2/2005 |
| JP | 2006525858 A | 11/2006 |
| JP | 4246020 B2 | 4/2009 |
| WO | 9932164 A1 | 7/1999 |
| WO | 03103553 A1 | 12/2003 |

* cited by examiner

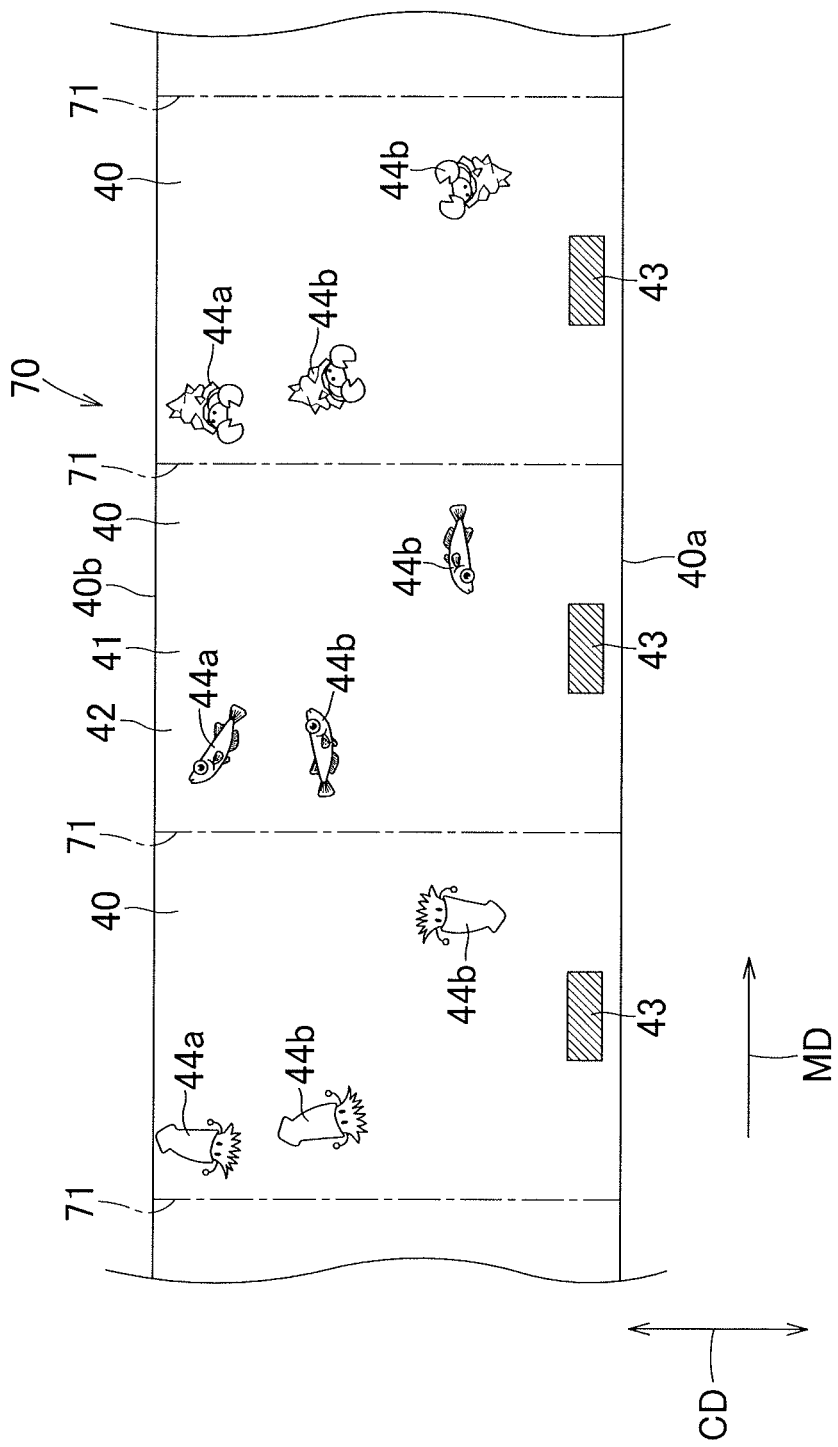

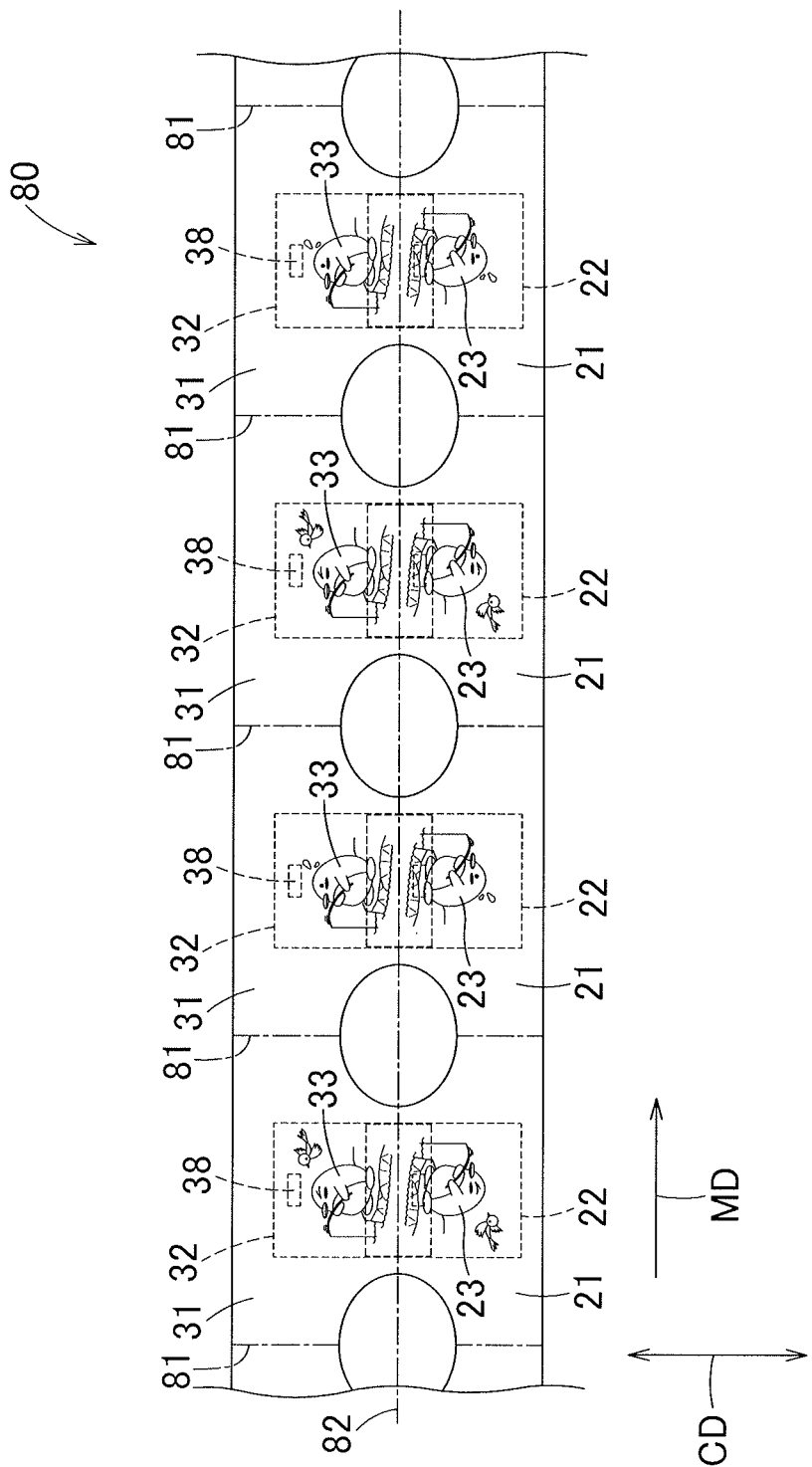

DISPOSABLE WEARING ARTICLE

RELATED APPLICATIONS

The present application is a National Phase of International Application Number PCT/JP2011/050664, filed Jan. 17, 2011, and claims priority from Japanese Application Number 2010-009520, filed Jan. 19, 2010.

TECHNICAL FIELD

The present invention relates to disposable wearing articles and more particularly to disposable wearing articles such as disposable toilet-training pants, disposable incontinent pants, disposable sanitary pants and the like.

BACKGROUND

Conventionally, disposable diapers each including a front waist member defining a front waist region, a rear waist member defining a rear waist region and a crotch member extending between the front and rear waist regions and defining a crotch region are known. For example, JP 2006-525858 A (PTL 1) discloses such a diaper in which the front and rear waist members are bonded to the outer surface of the crotch member which includes a patch sheet printed with graphics.

CITATION LIST

Patent Literature

{PTL 1} JP 2006-525858 A

SUMMARY OF INVENTION

Technical Problem

According to the disclosure of PTL 1, the graphic printed on the patch sheet can be visually recognized from the outside of the diaper by the wearer. However, the graphics which may be prevented or restricted from being visually recognized from the outside of the diaper are not disclosed therein.

An Object of the present invention is to provide a disposable wearing article having a position indicator mark formed on a crotch member and overlapped with front and rear waist members.

Solution to Problem

According to the present invention there is provided a disposable wearing article having a longitudinal direction and a transverse direction, including: a skin-facing side; a non-skin-facing side; a first waist region defined by one of front and rear waist regions; a second waist region defined by the other of the front and rear waist regions; a crotch region extending between the first and second waist regions; a first waist member defining at least the first waist region; a second waist member defining the second waist region and a crotch member defining at least the crotch region, wherein the first and second members are joined to the non-skin-facing side of the crotch member.

The features of the present invention reside in that:
the crotch member includes a printed sheet formed with a position indicator mark;
the printed sheet continuously extends in the longitudinal direction from a first end overlapping the first waist member to a second end overlapping the second waist member; and the mark overlaps at least one of the first and second waist members so that visual recognition of the mark from the non-skin-facing side is prevented or restricted.

According to one embodiment of the present invention, the printed sheet is formed of a liquid-impervious but moisture-pervious sheet and the crotch member includes the printed sheet and a backsheet lying on the non-skin-facing side of the printed sheet.

According to another embodiment of the present invention, the printed sheet is formed of one of a liquid-impervious but moisture-pervious plastic film, a fibrous nonwoven fabric or paper.

According to still another embodiment of the present invention, the crotch member includes a first overlapping region in which the first and second waist members overlap each other and an intermediate region extending in the longitudinal direction between these first and second overlapping regions, wherein the intermediate region is formed with a graphic element adapted to be visually recognized from the non-skin-facing side.

According to yet another embodiment of the present invention, at least one of the first and second waist members is formed with a graphic element adapted to be visually recognized from the non-skin-facing side.

According to further another embodiment of the present invention, the graphic elements represented on the first and second waist members are formed so as to overlap the first overlapping region and the second overlapping region.

According to an alternative embodiment of the present invention, the first and second waist sheets respectively include first and second waist sheets lying on the non-skin-facing side and liquid-impervious but moisture-pervious front and rear graphic plastic films, wherein the graphic element is formed on at least one of the front and rear graphic plastic films.

Advantageous Effects of Invention

According to some embodiments of the present invention, there is provided the position indicator marks on the printed sheet of the crotch member may be overlapped by at least one of the first and second waist members to ensure that these marks are prevented or restricted from being visually recognized from the outside of the wearing article. In this way, it is possible to prevent aesthetic properties of the wearing article from being deteriorated by these marks.

BRIEF DESCRIPTION OF DRAWINGS

FIG. 7 is a diagram illustrating a process of making the crotch member.

FIG. 8 is a diagram illustrating a process of making front and rear waist members.

DESCRIPTION OF EMBODIMENTS

Figure 1:
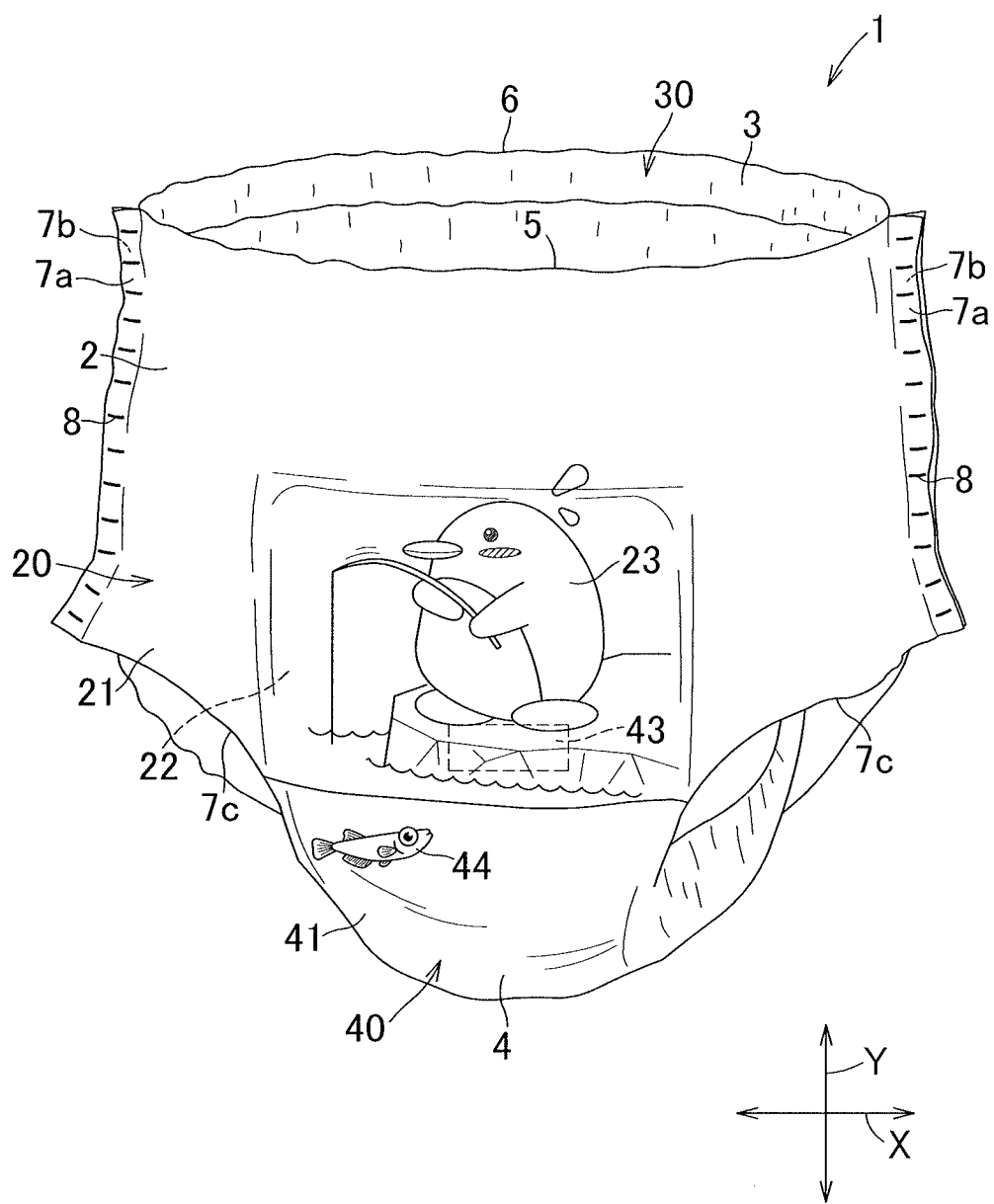
FIG. 1 is a perspective view of a disposable diaper as one example of disposable wearing articles according to the present invention.
Figure 2:
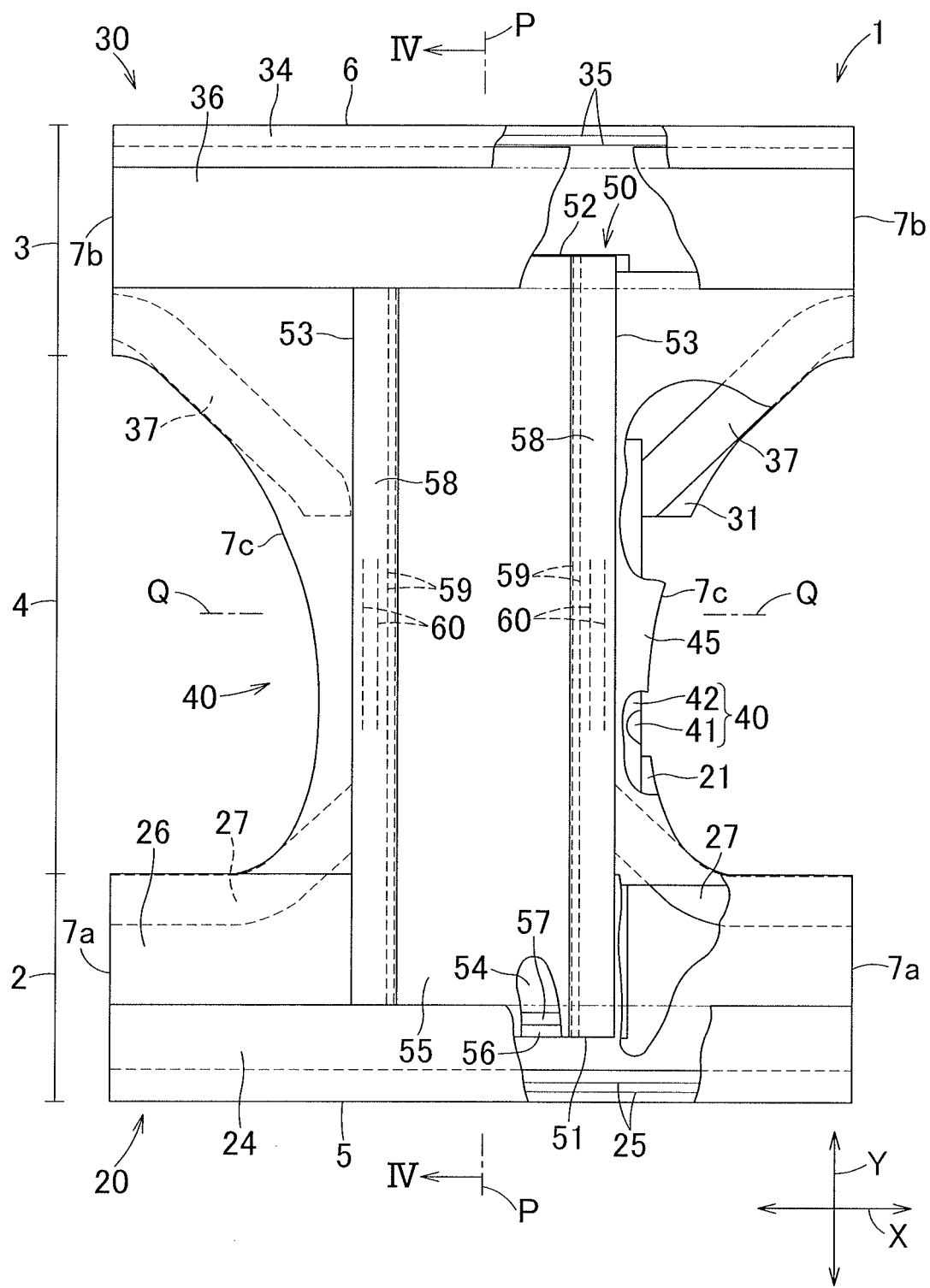
FIG. 2 is a partially cutaway developed view of the diaper.
Figure 3:
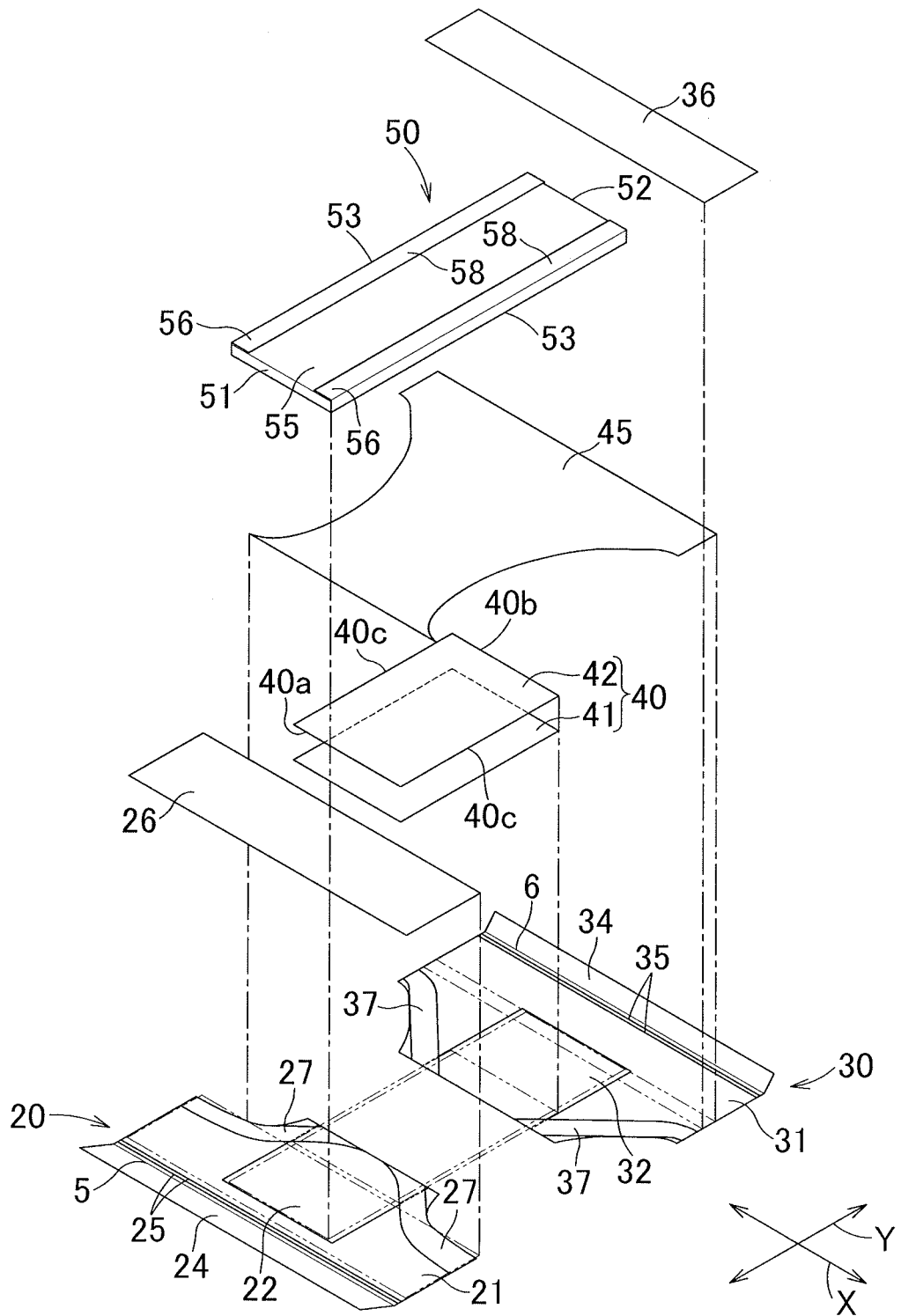
FIG. 3 is an exploded perspective view of the diaper.
Figure 4:
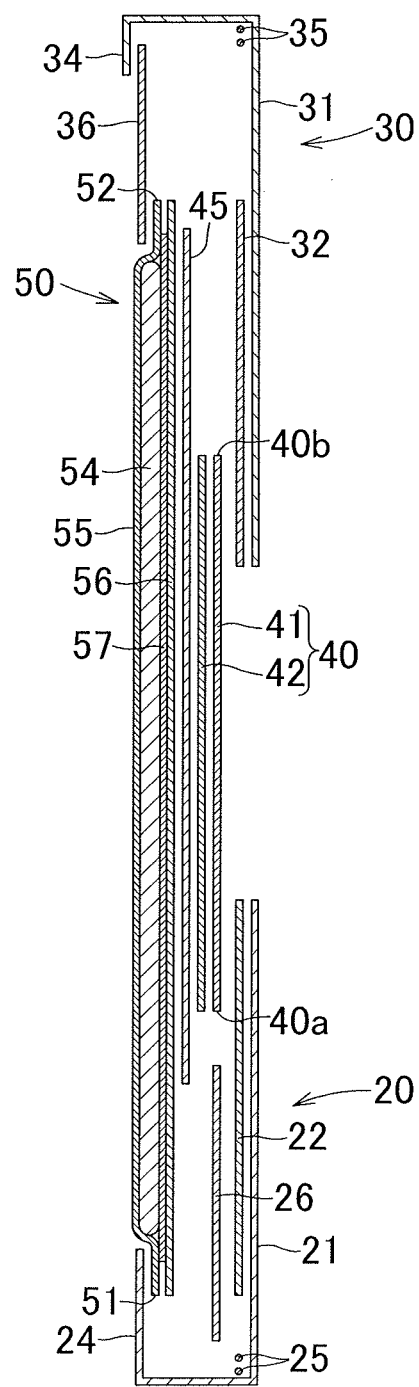
FIG. 4 is a schematic sectional view taken along line IV-IV in FIG. 2.

FIG. 1 is a perspective view of a disposable diaper 1 as one example of disposable wearing articles according to the present invention, FIG. 2 is a partially cutaway developed view of the diaper 1, FIG. 3 is an exploded perspective view of the diaper 1 and FIG. 4 is a schematic sectional view taken along line IV-IV in FIG. 2. The diaper 1 has an imaginary longitudinal center line P-P bisecting a length dimension in a transverse direction X, an imaginary transverse center line Q-Q bisecting a length dimension in a longitudinal direction Y and is substantially symmetric about the imaginary longitudinal direction Y.

The diaper 1 includes a skin-facing side and a non-skin-facing side, a front waist region 2, a rear waist region 3, a crotch region 4 extending between the front and rear waist regions 2, 3, front and rear ends 5, 6 opposed to each other about the imaginary transverse center line Q-Q and extending in the transverse direction X and side edges opposed to each other about the imaginary longitudinal direction P-P and extending in the longitudinal direction Y. The side edges are segmented into front side edges 7a lying in the front waist region 2, rear side edges 7b lying in the rear waist region 3 and crotch side edges 7c lying in the crotch region 4.

The front side edges 7a as well as the rear side edges 7b extend substantially in parallel to the imaginary longitudinal center line P-P and the crotch side edges 7c are concavely curved so as to be put in close contact about the wearer's thighs. The front side edges 7a and the rear side edges 7b are joined together by side seams 8 arranged intermittently in the longitudinal direction Y and thereupon a waist-opening and a pair of leg-openings are formed.

The diaper 1 includes a front waist member 20 defining the front waist region 2, a rear waist member 30 defining the rear waist region 3 and a crotch member 40 extending between these front and rear waist members 20, 30 in the longitudinal direction Y to define the crotch region 4.

The front and rear waist members 20, 30 respectively have substantially trapezoidal front and rear waist sheets 21, 31 and front and rear graphic films 22, 32 bonded to respective inner surfaces of the front and rear waist sheets 22, 32 by bonding means such as hot melt adhesives, heat bond and sonic bond. The front and rear graphic plastic films 22, 32 are respectively formed with front and rear graphic elements 23, 33, for example, graphics of penguin. These graphic elements 23, 33 are formed on respective surfaces of the front and rear graphic plastic films 22, 32 facing the front and rear waist sheets 21, 31 so that the graphics may be visually recognized from the non-skin-facing side of the diaper 1 through the front and rear waist sheets 21, 31.

The front and rear waist sheets 21, 31 are formed of spun bonded fibrous nonwoven fabric having the fibrous layer preferably made of crimped spun bonded filament fibers. Use of such crimped fibers advantageously facilitates the waist sheets 21, 31 to come in close contact with the wearer's body and improves the texture since the crimped spun bonded filament fibers have high elastic stretch properties. On the other hand, in order to ensure that the front and rear graphic elements 23, 33 can be visually recognized as has been described above, the front and rear waist sheets 23, 33 having total luminous transmittance in a range of about 60 to 100%, preferably in a range of about 70 to 80% may be prepared. The total luminous transmittance maybe measured by Color Difference Meter (Color Difference Meter Of Flicker Photometer Type Z-300A manufactured by Nippon Denshoku Industries Co., Ltd in Japan and obtained TT-value may be determined as the total luminous transmittance (%).

The front and rear graphic plastic films 22, 32 are formed of a liquid-impervious but moisture-pervious plastic film and attached to the front and rear waist sheets 21, 31 in the vicinity thereof as viewed in the transverse direction X.

The crotch member 40 includes a front end 40a extending in the transverse direction X and overlapping the front waist member 20, a rear end 40b overlapping the rear waist member 30 and opposite side edges 40c extending in the longitudinal direction Y. The crotch member 40 includes a backsheet 41 lying on the non-skin-facing side and facing the front and rear waist sheets 21, 31 and a printed sheet 42 overlapped on the side of the backsheet 41 facing the wearer's body.

The backsheet 41 may be formed of a moisture-pervious fibrous nonwoven fabric and the printed sheet 42 may be formed of a flexible sheet such as a liquid-impervious but moisture-pervious plastic film sheet, a fibrous nonwoven fabric or paper. The backsheet 41 and the printed sheet 42 are substantially the same in shape as well as in size and bonded to each other by bonding means such as hot melt adhesives.

Figure 5:
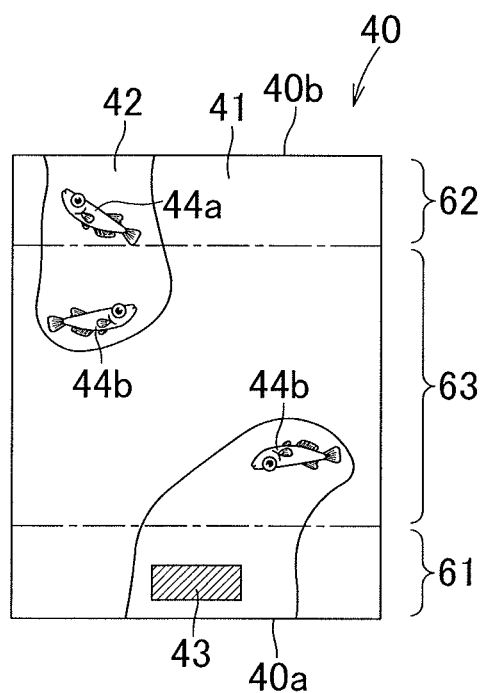
FIG. 5 is a partially cutaway plan view of a crotch member as viewed from the non-skin-facing side.

FIG. 5 illustrates the crotch member 40 from the side of the backsheet 41 and is partially cutaway for convenience of illustration. The side of the printed sheet 42 facing the backsheet 41 is formed with a position indicator mark 43 and crotch graphic elements 44a, 44b such as graphics of fish. The position indicator mark 43 as well as the crotch graphic elements 44a, 44b can be visually recognized through the backsheet 41. This backsheet 41 is prepared like the front and rear waist sheets 21, 31 to have the total luminous transmittance in a range of about 60 to about 100%, preferably in a range of about 70 to about 80%.

The position indicator mark 43 is used to check the positions at which the crotch members 40 continuously fed into the transverse direction X are cut off into the individual crotch members 40 for the individual diapers in a process of manufacturing of them. The position indicator mark 43 is formed in the vicinity of the front end 40a substantially at midspan as viewed in the transverse direction. The crotch graphic elements 44a, 44b are respectively formed in the vicinity of the rear end 40b and inside the position indicator mark 43 as viewed in the longitudinal direction Y.

As shown in FIGS. 2 and 3, a fixing sheet 45 formed of a fibrous nonwoven fabric is attached to the crotch member 40 so as to cover the entire area thereof. The fixing sheet 45 is overlapped on the printed sheet 42 and bonded thereto by bonding means such as hot melt adhesives, heat bond and sonic bond. The fixing sheet 45 has a width dimension larger than that of the crotch member 40 and extends across the crotch region 4 into the rear waist region 3. Similarly to the front and rear sheets 21, 31, the backsheet 41 and the fixing sheet 45 may be formed of spun bonded fibrous nonwoven fabric made of crimped fibers or formed of an inelastic air-through fibrous nonwoven fabric.

The front and rear waist members 20, 30 and the crotch member 40 as have been described above are provided on the respective skin-facing sides with a liquid-absorbent structure 50 extending across the crotch region 4 into the front and rear waist regions 2, 3 and attached by bonding means such as hot melt adhesives, heat bond and sonic bond. The liquid-absorbent structure 50 has a transversely long rectangular shape contoured by front and rear ends 51, 52 extending in the transverse direction X and opposite side edges 53 extending in the longitudinal direction Y. The front end 51 overlaps the front waist member 20, the rear end 52 overlaps the rear waist member 30 and an intermediate section between these front and rear ends 51, 52 overlaps the crotch member 40.

The liquid-absorbent structure 50 includes a liquid-absorbent core 54 formed, for example, by wrapping a mixture of fluff pulp fibers and super-absorbent polymer particles with a liquid-dispersant sheet (not shown), a liner 55 lying on the skin-facing side to cover an upper surface of the liquid absorbent core 54, a cover sheet 56 covering a bottom surface of the liquid-absorbent core 54 and a leakage-barrier sheet 57 made of a plastic material and interposed between the cover sheet 56 and the liquid-absorbent core 54.

The cover sheet 56 extends outward in the transverse direction X beyond the side edges of the liquid-absorbent core 54 and partially folded back toward the imaginary longitudinal center line P-P to form a pair of sleeve-like side flaps 58, 58. Within the respective side flaps 58, 58, strand-like elastic elements 59, 60 extending in the longitudinal direction Y are attached under tension and in a contractible manner. The two or more elastic elements 59 lying inside as viewed in the transverse direction X extend across the crotch region 4 into the front and rear waist regions 2, 3. Under contraction of these elastic elements 59, the laterals of the cover sheet 56 are spaced from the liner 55 lying on the skin-facing side to form barrier- or gasket-cuffs adapted to prevent sideways leakage of body waste. The two or more elastic elements 60 lying outboard of the elastic elements 59 as viewed in the transverse direction X are attached only to the middle zone of the crotch region 4 to form belt-like elastic zones extending along the wearer's inguinal regions.

In the front waist region 2, the front waist sheet 21 is folded back along the front end 5 toward the imaginary transverse center line Q-Q to form a front end flap 24. In a similar fashion, in the rear waist region 3, the rear waist sheet 31 is folded back along the rear end 6 toward the imaginary transverse center line Q-Q to form a rear end flap 34. Within these front and rear flaps 24, 34, a plurality of the front waist elastic yarns or threads 25 and a plurality of the rear waist elastic yarns or threads 35 are attached under tension and in contractible manner in the transverse direction X. Specifically, these front and rear waist elastic yarns or threads 25, 35 are respectively bonded to the front and rear end flaps 24, 34 by bonding means such as hot melt adhesives (not shown).

Front and rear waist region elastic sheets 26, 36 are contractibly attached under tension in the transverse direction X inside the front and rear waist sheets 21, 31. The front and rear waist region elastic sheets 26, 36 are formed of elastically stretchable fibrous nonwoven fabric containing elastomeric fibers. The front waist elastic sheet 26 lying in the front waist region 2 is interposed between the bottom surface of the liquid-absorbent structure 50 and the front waist sheet 21 and contractibly attached under tension and in the transverse direction X. The front waist region elastic sheet 26 has its outer surface bonded to the front waist sheet 21 by bonding means such as hot melt adhesives (not shown) and its inner surface bonded to the cover sheet 56.

The rear waist region elastic sheet 36 lying on the side of the working surface of the liquid-absorbent structure 50 and contractibly attached thereto under tension and in the transverse direction X. The respective both side edges of the front and rear waist region elastic sheets 26, 36 overlap the respective both side edges of the front and rear waist sheets 21, 31. The rear waist region elastic sheet 36 extends outward beyond the rear end 52 of the liquid-absorbent structure 50 in the longitudinal direction Y to cover the rear end 52 and extends outward also in the transverse direction X beyond the side edges of the liquid-absorbent structure 50. Outside the liquid-absorbent structure 50 in the transverse direction X, the rear waist region elastic sheet 36 and the rear waist sheet 31 are bonded together over a whole area thereof by bonding means such as hot melt adhesives (not shown).

The front and rear end flaps 24, 34 formed by folding back the front and rear waist sheets 21, 31 are bonded to the respective inner surfaces of the front and rear waist region elastic sheets 26, 36. The front end flap 24 having its inner end 21a covering the front end 51 of the liquid-absorbent structure 50 is bonded over its whole area to the front waist region elastic sheet 26 and the liquid-absorbent structure 50 by bonding means such as hot melt adhesives (not shown). The front end 51 is covered with the front waist sheet 21 and bonded thereto to prevent the component material of the liquid-absorbent core 54 such as fluff pulp fibers from falling off.

An inner end 31a of the rear end flap 34 slightly overlaps the rear waist region elastic sheet 36 and is bonded over its whole area thereto by bonding means such as hot melt adhesives (not shown).

In the diaper 1 of the construction as has been described above, the front and rear waist region elastic sheets 26, 36 respectively have sizes corresponding to substantially whole areas of the front and rear waist regions 2, 3 and are contractibly provided under tension in the front and rear waist regions 2, 3, respectively. With such arrangement, substantially whole areas of the front and rear waist regions 2, 3 can be put in contact with the wearer's body at an appropriately high fit. By using the front and rear waist region elastic sheets 26, 36, the waist regions can be put in close contact, over a wide range, with the wearer's body at the desirably high fit and, at the same time, slipping down of the diaper 1 can be prevented.

Respective sections of the front and rear waist sheets. 21, 31 adjacent the crotch region 4 are provided on respective inner surfaces thereof and along the crotch side edges 7c, 7c with the front and rear leg elastic elements 27, 37 contractibly attached under tension. These front and rear leg elastic elements 27, 37 are formed of elasticized sheets or an elastically stretchable fibrous nonwoven fabric containing elastomeric fibers. The fixing sheet 45 is overlapped on part of the front leg elastic elements 27 and the entirety of the rear leg elastic elements 37 to fix these elastic elements. These front and rear leg elastic elements 27, 37 serve to put the leg-openings in close contact about the wearer's legs.

The front and rear waist region elastic sheets 26, 36 may be formed of an elastic fibrous nonwoven fabric made of heat-sealable elastomeric fibers having a mass per unit area of about 20 to about 50 $g/m^2$, preferably about 30 to about 40 $g/m^2$ and a fiber density of about 0.01 to about 0.04 $g/cm^3$, preferably about 0.025 to about 0 035 $g/cm^3$. More specifically, the sheets 51, 52 may be formed of a fiber blend of thermoplastic polyurethane polymers and thermoplastic polymer other than the thermoplastic polyurethane polymers, for example, polyolefin polymers such as styrene elastomers, polyolefin elastomers, vinyl chloride elastomers, amide elastomers, polyethylene, polypropylene, and polystyrene.

It is also possible to form the front and rear waist region elastic sheets 26, 36 by a fiber blend of elastomeric fibers and non-elastomeric fibers. Use of the fiber blend makes it possible to reduce friction against the wearer's skin due to the elastomeric fibers. In other words, the non-elastomeric fibers constituting the fiber blend serves to improve slippage of these front and rear waist region elastic sheets 26, 36 on the wearer's skin and thereby to improve the softness as well as the texture of these front and rear waist region elastic sheets 26, 36. It is also possible to adjust the stretch properties of the front and rear waist region elastic sheets 26, 36.

The front and rear waist sheets 21, 31 may be formed of heat-sealable spun bonded fibrous nonwoven fabric having a mass per unit area of about 15 to about 40 $g/m^2$, preferably about 25 to 35 $g/m^2$ and a fiber density about 0.06 to about 0.10 $g/cm^3$, preferably about 0.07 to about 0.09 $g/cm^3$. It is also possible to form these front and rear waist sheets 21, 31 of two or more layers, respectively.

Figure 6:
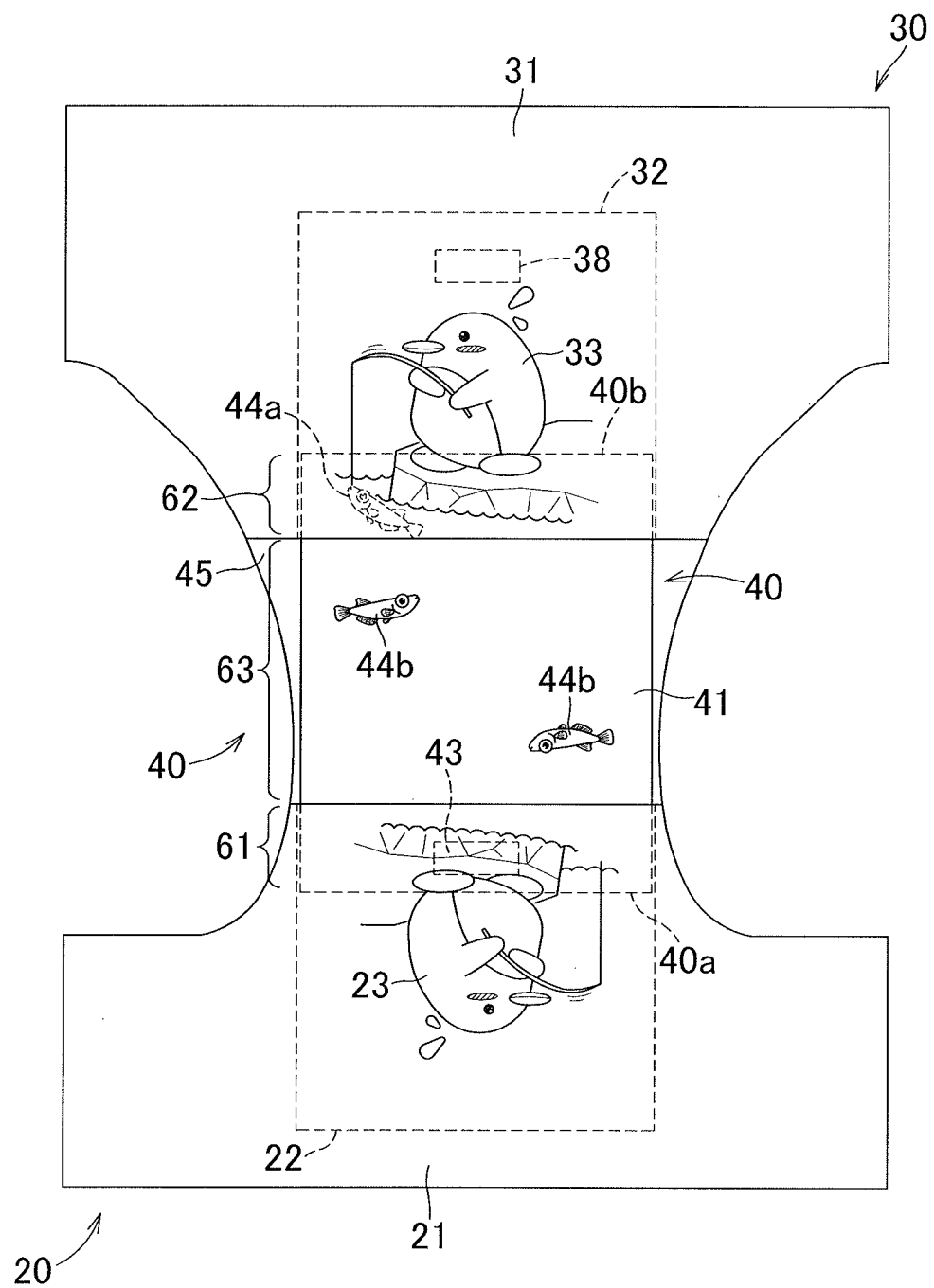
FIG. 6 is a diagram illustrating an outer appearance of the diaper.

In the diaper 1 constructed as has been described above, as shown in FIG. 6, the front and rear ends 40a, 40b of the crotch member 40 are overlapped by and bonded to the front and rear waist members 20, 30 to define first and second overlapping regions 61, 62, respectively, and an intermediate region 63 extending between these first and second overlapping regions 61, 62. Referring to FIGS. 5 and 6, the first overlapping region 61 is provided with the position indicator mark 43, the second overlapping region 62 is provided with a graphic of fish as the crotch graphic element 44a and the intermediate region 63 is provided with a graphic of fish as the crotch graphic element 44b. The position indicator mark 43 is used to detect the position at which the continuous web of crotch members 40 is cut to obtain the individual crotch members 40 and usually attaches no importance to its aesthetic effect but rather there is a possibility that its exposure on the diaper's appearance might cause disfigurement of the diaper.

To avoid such a problem, the first overlapping region 61 is covered with the front waist sheet 21 and the front graphic film 22 of the front waist member 20 according to the present embodiment. In this way, at least it can be restricted that the position indicator mark 43 might be visually recognized from the outside. In addition, a penguin is portrayed on the front graphic film 22 as the front graphic element 23 so that this front graphic element 23 may overlap the position indicator mark 43 and thereby further reliably restrict visual recognition of the position indicator mark 43 from the outside. With this unique arrangement, the position indicator mark 43 should not disfigure the diaper.

On the rear graphic film sheet 32 of the rear waist member 30, a penguin holding a fishing rod is portrayed as the rear graphic element 33. The rear graphic film 32 is overlapped with the rear waist sheet 31 having the so high total luminous transmittance as previously mentioned and therefore the rear graphic element 33 can be visually recognized through the rear waist sheet 31. On the second overlapping region 62 of the crotch member 40, a graphic of fish is portrayed as the crotch graphic element 44a. This graphic of fish is set out so that this fish is positioned on a distal end of the fishing line included in the rear graphic element 33 and can be visually recognized through the rear waist member 30 when the rear waist member 30 overlaps the crotch member 40. It should be understood here that this graphic of fish as the crotch graphic element 44a is made appropriately smudgy by the rear waist member 30 to be appeared as if this fish is taking the hook. By making the crotch graphic element 44a appropriately smudgy, various modes of graphic can be represented.

In order that the crotch graphic element 44a can be visually recognized through the rear waist member 30 even if in smudgy condition, the rear waist member 30 should have a total luminous transmittance of about 60 to about 100%, preferably about 70 to about 80% in its section overlapped on the rear graphic film sheet 32 and not having the rear graphic element 33. The total luminous transmittance was measured in the same manner as in the case of the front and rear waist sheets 21, 31 themselves. If the total luminous transmittance is 60% or lower, the crotch graphic element 44a of the crotch member 40 covered with the front and rear waist sheets 21, 31 may not be visually recognized at all. According to the present embodiment, the front waist member 20 has the same total luminous transmittance of the rear waist member 30.

The intermediate region 63 of the crotch member 40 is provided with a graphic of another fish as the crotch graphic element 44b. The front waist member 20 overlapping the crotch member 40 in the first overlapping region 61 is provided with a graphic of penguin so that the graphic of another fish as the crotch graphic element 44b is spaced from the fishing line extending downward from the fishing rod. These crotch graphic elements 44a, 44b portrayed in the intermediate region 63 can be visually recognized as has previously described.

In the front waist region 2 of such diaper 1, the position indicator mark 43 is provided in the first overlapping region 61 and overlapped by the front graphic element 23 to prevent this position indicator mark 43 from being visually recognized from the side of the diaper 1 facing the wearer's garment, i.e., from the outside of the front waist sheet 21. The region in which the front graphic element 23 and the position indicator 43 overlap each other, the total luminous transmittance is sufficiently reduced in comparison to the remaining region to prevent the position indicator mark 43 from being visually recognized. The total luminous transmittance of the front waist member 20 in the region formed with the front graphic element 23 may be in a range of about 0 to about 60%, preferably about 0 to about 30%.

In the rear waist region 3, after the crotch graphic element 44a has been set out, the rear waist graphic element 33 may be set out so as not to overlap the crotch graphic element 44a to enjoy a combination of the crotch graphic element 44a and the rear waist graphic element 33. More specifically, in the front waist region 2, the front waist member 20 represents a penguin still not getting fish as the front graphic element 23 while covering over the position indicator mark 43 in the front waist region 2, a pair of fish freely swimming in the sea are represented as the crotch graphic elements 44b in the crotch region 4 and a penguin having got a fish is represented as the combination of the rear graphic element 33 and the crotch graphic element 44a in the rear waist region 3.

While the case in which the front graphic element 23 and the position indicator mark 43 are overlapped each other to make the position indicator mark 43 invisible has been exemplarily described, it is also possible to make the position indicator mark 43 invisible or substantially invisible merely by setting the total luminous transmittance of the front waist member 20 to an appropriately low level without overlapping the position indicator mark 43 with the front graphic element 23. It is also possible to place the position indicator mark 43 in the second overlapping region 62.

While the case in which the crotch graphic element 44a becomes difficult to be visually recognized in the rear waist member 30 has been exemplarily described, the present invention is not limited to such arrangement but it is possible to implement the present invention so that the crotch graphic element 44a becomes perfectly invisible due to overlapping of the rear waist member 30. The invention may be implemented in further another arrangement such that the crotch graphic elements 44a are difficult to be visually recognized in one of the waist members and the crotch graphic elements 44a may not visually recognized at all in the other waist member. According to such embodiment, different conditions, i.e., the condition that the crotch graphic elements 44a are not visually recognizable, the condition that the crotch graphic elements 44a are difficult to be visually recognized and the condition that the crotch graphic elements 44a are clearly visible may be selectively created. Furthermore, the first overlapping region 61, the second overlapping region 62, the intermediate region 63, the front graphic film 22 and the rear graphic film 32 may be provided with different graphics, respectively, to represent graphics of ample variation.

According to the present embodiment, graphics are portrayed as the graphic elements not only in the front and rear waist members 20, 30 but also in the crotch region 40, allowing the graphics to be portrayed in a wider area and the respective graphics portrayed on the respective members to be combined one with another and thereby allowing picture of ample variation to be created.

While the case in which the position indicator mark 43 is formed in the first overlapping region 61 so as not to be visually recognized has been exemplarily described, in addition to the position indicator mark 43, production number, lot number or the like may be provided in the first overlapping region 61. With the diaper 1 put on the wearer's body, these numbers are covered with the front waist member 20 and not visible from the outside but become visible by peeling off the front waist member 20. Specifically, the first and/or second overlapping regions 61, 62 may be provided with numbers or the like adapted to become visually recognizable by peeling off the front and/or rear waist members 20, 30 as the need arises.

FIG. 7 is a diagram illustrating a method for making the crotch member 40. The individual crotch member 40 is obtained by cutting a web 70 being continuous in a machine direction MD along cutting lines 71. The web 70 includes the backsheet 41 and the printed sheet 42 both constituting component elements of the crotch member 40 and laminated together in this web 70. The cutting lines 71 extending in a cross direction CD which is orthogonal to the machine direction MD. The printed sheet 42 is provided with the position indicator marks 43 and the crotch graphic elements 44a, 44b. As the crotch graphic elements 44a, 44b, three (3) kinds of graphics, for example, calamary, fish and shellfish are prepared and arranged in this order in the machine direction MD.

The web of crotch member 40 as has been described above is cut off into the individual crotch members 40 by cutter means (not shown) adapted to operate upon receipt of a mark detection signal from means (not shown) to detect the position indicator mark 43. The web 70 adapted to form the individual crotch members 40 can be successively cut off along the given cutting lines 71 upon detection of the position indicator marks 43.

FIG. 8 is a diagram illustrating a method for making the front and rear waist members 20, 30. The front and rear waist members 20, 30 are obtained by cutting off a web 80 being continuous in the machine direction MD along cutting lines 81. More specifically, the web 80 including the front and rear waist sheets 21, 31 continuously arranged in the machine direction MD and the front and rear graphic film 22, 32 respectively formed with the front and rear graphic elements 23, 33 bonded thereto. The front waist sheet 21 and the rear waist sheet 31 are contiguous to each other in the cross direction CD and each pair of the front and rear waist sheets 21, 31 is obtained by cutting off the web 80 along a cutting line 82 extending in parallel to the cross direction CD.

The respective pairs of front and rear waist sheets 21, 31 being continuously arranged in the machine direction MD are cut off, like in the case of the crotch member 40, along the cutting lines 81 extending in the machine direction MD upon detection of the position indicator mark 38. The front waist sheet 21 and the rear waist sheet 31 are arranged to be paired and contiguous to each other in the cross direction CD and therefore the position indicator mark 38 may be formed on one of the front and rear waist sheets 21, 31. The web 80 may be cut off along the cutting lines 81 and then along the cutting line 82 to separate the front and rear waist sheets 21, 31 from each other or vice versa. In both cases, the position indicator mark 38 may be formed on one of the front and rear waist sheets 21, 31 since the front and rear waist sheets 21, 31 are integrated in the cross direction CD.

The front and rear graphic elements 23, 33 portrayed on the front and rear waist members 20, 30 may have a pattern A including graphics of penguin and bird and a pattern B including penguin only and these patterns A, B are alternately arranged in the machine direction MD. Three patterns, i.e., calamary, fish and shellfish are arranged in the machine direction MD of the web in this order. With such arrangement, the front and rear waist members 20, 30 obtained by cutting off the web 70 may be combined with the crotch members 40 obtained by cutting off the web 80 to form the diapers 1 so that each pair of the adjacent diapers 1 may have pictures different from each other. For example, the picture including a combination of the pattern A of the front and rear graphic elements 23, 33 and calamaries of the crotch graphic elements 44a, 44b, or a combination of the pattern B and fish may be obtained.

Two (2) kinds of picture are prepared for the front and rear graphic elements 23, 33 and three (3) kinds of picture are prepared as the crotch graphic elements 44a, 44b. Inconsequence, the patterns of combination may be increased when the web 80 is cut off to form the front and rear waist members 20, 30, then the web 70 is cut off to form the crotch members 40 and the front and rear waist members 20, 30 are bonded to the crotch members 40 in the order of cutting operations to form the individual diapers 1. Specifically, the pictures as the graphic elements repetitively appear in the order of the pattern A and the pattern B on the front and rear waist members 20, 30 and correspondingly the pictures as the graphic elements on the crotch members 40 repetitively appear in the order of calamary, fish and shellfish. For every go-around of the pictures of calamary, fish and shellfish, the patterns A, B corresponding to calamary, fish and shellfish are displaced one by one. Consequentially, the combination of the pictures displaced on the diaper 1 becomes ample, for example, combination of pattern A and calamary, combination of pattern B and fish, combination of pattern A and shellfish, combination of pattern B and calamary, combination of pattern A and fish, and combination of pattern B and shellfish. Merely by repeating the graphic elements in a desired order and thereby varying the number of the front and rear graphic elements and the crotch graphic elements, the number of combinations can be increased. The number of combinations is equal to the least common multiple of the number of kinds of the front and rear graphic elements and the number of kinds of the crotch graphic elements. The number of kinds of the front and rear graphic elements as well as of the crotch graphic elements is not limited to the number as has been described just above and may be selectively set.

As materials for the respective component members or elements of the elasticized waist panel 11 and the crotch member 12 are not limited to those which have been described with respect to the first and second embodiments of the present invention and the other various materials widely used in the related technical field may be selectively used without departing from the scope of the present invention.

As used herein the terms "first" and "second" and the appended Claims should be construed to be used for the purpose of merely discriminating elements and/or positions of the same appellation. For example, as used the term "first waist region" means one of the front and rear waist regions and the term "second waist region" means the other thereof.

REFERENCE SIGNS LIST 1 diaper (disposable wearing article)
2 front waist region (first or second waist region)
3 rear waist region (first or second waist region)
4 crotch region
8 side seams 20 front waist member (first or second waist member)
21 front waist sheet (first or second waist sheet)
22 front display film (first or second display film)
23 front display element (display element)
30 rear waist member (first or second waist member)
31 rear waist sheet (first or second waist sheet)
32 rear display film (first or second display film)
33 rear display element (display element)
40 crotch member
40a front end (first or second end)
40b rear end (first or second end)
41 backsheet
42 printed sheet
43 position indicator mark
44a crotch display element (display element)
44b crotch display element (display element)
61 first overlapping region
62 second overlapping region
63 intermediate region

The invention claimed is:

1. A disposable wearing article having a longitudinal direction and a transverse direction, said disposable wearing article comprising:
 a skin-facing side;
 a non-skin-facing side;
 a first waist region;
 a second waist region;
 a crotch region extending between the first and second waist regions;
 a first waist member defining at least the first waist region;
 a second waist member defining the second waist region; and
 a crotch member defining at least the crotch region,
 wherein
 the first and second waist members are joined to the non-skin-facing side of the crotch member,
 the crotch member comprises a printed sheet formed with a position indicator mark,
 the printed sheet continuously extends in the longitudinal direction from a first end overlapping the first waist member to a second end overlapping the second waist member,
 the position indicator mark overlaps at least one of the first and second waist members and is not visually recognizable from the non-skin-facing side,
 the printed sheet further includes a graphic element, and
 the graphic element and the position indicator mark are formed on a same side of the printed sheet.

2. The disposable wearing article defined by claim 1, wherein
 the printed sheet is formed of a liquid-impervious but moisture-pervious sheet, and
 the crotch member includes the printed sheet and a backsheet lying on the non-skin-facing side of the printed sheet.

3. The disposable wearing article defined by claim 1, wherein the printed sheet is formed of a liquid-impervious but moisture-pervious plastic film, a fibrous nonwoven fabric or paper.

4. The disposable wearing article defined by claim 1, wherein the crotch member comprises
 a first overlapping region overlapping the first waist member;
 a second overlapping region overlapping the second waist member; and
 an intermediate region extending in the longitudinal direction between these first and second overlapping regions,
 wherein the intermediate region is formed with the graphic element visually recognizable from the non-skin-facing side.

5. The disposable wearing article defined by claim 4, wherein at least one of the first and second waist members is formed with another graphic element that is visually recognizable from the non-skin-facing side.

6. The disposable wearing article defined by claim 5, wherein the another graphic element represented on the first and second waist members includes a first graphic element and a second graphic element overlapping the first overlapping region and the second overlapping region.

7. The disposable wearing article defined by claim 5, wherein
 the first and second waist members respectively comprise first and second waist sheets lying on the non-skin-facing side, and
 the first and second waist sheets are formed of liquid-impervious but moisture-pervious front and rear graphic films at least one of which defines the another graphic element.

* * * * *